United States Patent [19]
Weiner et al.

[11] Patent Number: 6,087,486
[45] Date of Patent: Jul. 11, 2000

[54] NUCLEOTIDE SEQUENCES ENCODING VPR RECEPTOR PROTEIN

[75] Inventors: David B. Weiner, Merion; Velpandi Ayyavoo, Havertown; Sundarasama Mahalingham, Philadelphia; William V. Williams, Havertown, all of Pa.

[73] Assignee: The Trustees of the University of Pennsylvania, Philadelphia, Pa.

[21] Appl. No.: 09/014,877

[22] Filed: Jan. 28, 1998

Related U.S. Application Data

[63] Continuation of application No. 08/593,695, Jan. 29, 1996, abandoned.

[51] Int. Cl.$^7$ ............................ C07H 21/04; C12P 21/06; C12N 15/00; C12N 1/20
[52] U.S. Cl. .................... 536/23.5; 435/69.1; 435/320.1; 435/252.3; 530/388.35
[58] Field of Search .................... 536/23.5; 435/69.1, 435/320.1, 252.3; 530/388.35

[56] References Cited

U.S. PATENT DOCUMENTS 5,001,230  3/1991  Brown et al. .............................. 536/27

OTHER PUBLICATIONS

Adachi, et al., "Production of Acquired Immunodeficiency Syndrome—Associated Retrovirus in Human and Nonhuman Cells Transfected with an Infectious Molecular Clone", *J. Virology*, Aug. 1986, 59, 284–291.

Aguanno, et al., "12–O–Tetradecanoylphorbol–13–Acetate–induced Differentiation of a Human Rhabdomyosarcoma Cell Line", *Cancer Res.*, 1990, 50, 3377–3382.

Arya, Suresh K. et al., "Trans–Activator Gene of Human T–Lymphotropic Virus Type III (HTLV–III)", *Science*, 1985, 229,69–73.

Chantal Petit, A.J. et al. "Human Immunodeficiency Virus Infection Down–Regulates HLA Class II Expression and Induces Differentiation in Promonocytic U937 Cells", *J. Clin. Invest.*, Jun. 1987, 79, 1883–1889.

Cohen, E.A. et al., "Identification of HIV–1 vpr product and function", *J. AIDS*, 1990, 3, 11–18.

Cohen, E.A. et al., "Human immunodeficiency virus vpr, product is a virion–associated regulatory protein", *J. Virol.*, 1990, 64, 3097–3099.

Colmenares et al., "The ski Oncogene Induces Muscle Differentiation in Quail Embryo Cells", *Cell*, 1989, 59, 293–303.

Connor, R. et al., "Vpr is Required for Efficient Replication of Human Immunodeficiency Virus Type–1 in Mononuclear Phagocytes", *Virology*, 1995, 206, 935–944.

Dedera et al., "Viral Protein R of Human Immunodeficiency Virus Types 1 and 2 Is Dispensable for Replication and Cytopathogenicity in Lymphoid Cells", *J.Virol.*, 1989, 63, 3205–3208.

Fields, S. and Song, "A Novel Genetic System to Detect Protein–Protein Interactions", *Nature*, 1989, 340, 245–246.

Fields, S., "The Two–Hybrid System to Detect Protein–Protein Interactions", *Methods: A Companion to Methods in Enzymology*, 1993, 5, 116–124.

Fields, S. and Sternglanz, "The Two–Hybrid System: An Assay for Protein–Protein Interactions", *Trends in Genetics (TIG)*, Aug. 1994, 10(8), 286–292.

Fisher, et al., "A Molecular Clone of HTLV–III with Biological Activity", *Nature*, 1985, 316, 262–265.

Frigerio et al., "Cloning, sequencing and expression of the L5, L21, L27a, L28, S5, S9, S10 and S29 human ribosomal protein mRNAs", *Biochim. Et Biophy. Acta*, 1995, 1262, 64–68.

Gallo, et al., "Frequent Detection and Isolation of Cytopathic Retroviruses (HTLV–III) From Patients with AIDS and at Risk for AIDS", *Science*, 1984, 224, 500–503.

Garrett, et al., "Rev Activates Expression of the Human Immunodeficiency Virus Type 1 vif and vpr Gene Products", *J. Virol.*, 1991, 65,1653–1657.

Gras–Masse, et al., "A Synthetic Protein Corresponding to the Entire VPR Gene Product form the Human Immunodeficiency Virus HIV–1 is Recognized by Antibodies from HIV–Infected Patients", *Int. J. Peptide Protein Res.*, 1990, 36, 219–226.

Griffin, et al., "Activation of HIV Gene Expression During Monocyte Differentiation by Induction of NF–kB", *Nature*, 1989, 339, 70–73.

Harada, S. et al., "Tumor promoter, TPA, enhances replication of HTLV–III/LAV", *Virology*, 1986, 154, 249–258.

Hattori, N. et al., "The human immunodeficiency virus type 2 vpr gene is essential for productive infection of human macrophages", *Proc. Natl. Acad. Sci. USA*, 1990, 87, 8080–8084.

He, J. et al., "Human Immunodeficiency Virus Type 1 Viral Protein R (Vpr) Arrests Cells in the $G_2$ Phase of the Cell Cycle by Inhibiting $p34^{cdc2}$ Activity", *J. Virology*, 1995, 69(11), 6705–6711.

Heinzinger, N. et al., "The Vpr Protein of Human Immunodeficiency Virus Type 1 Influences Nuclear Localization of Viral Nucleic Acids in Nondividing Host Cells", *PNAS USA*, 1994, 91, 7311–7315.

Hiti, A. et al., "Expression of the MycoD1 Muscle Determination Gene Defines Differentiation Capability But Not Tumorigenicity of Human Rhabdomyosarcomas", *Mol. Cell. Biol.*, 1989, 9(11), 4722–4730.

Janel, G. et al., "Localization of the VPR Gene Product in SIVmac Infected Cells", *Fifth International Conference on AIDS*, Montreal, Jun. 4–9, 1989, Abstract T.C.O. 45.

Korber, B. and Myers, "Signature Pattern Analysis: A Method for Assessing Viral Sequence Relatedness", *AIDS Res. Human Retrovirus*, 1992, 8(9), 1549–1560.

(List continued on next page.)

*Primary Examiner*—Mankvel Park
*Attorney, Agent, or Firm*—Woodcock Washburn Kurtz Mackiewicz & Norris LLP

[57] ABSTRACT

DNA molecules which encode rip-1 protein sequences are disclosed. Expression vectors and host cells which include the DNA molecules are disclosed.

20 Claims, No Drawings

OTHER PUBLICATIONS

Kozak, M., "Point mutations define a sequence flanking the AUG initiator codon that modulates translation by eukaryotic ribosomes", *Cell*, 1986, 44, 283–292.

Levy, D. et al., "Extracellular Vpr Protein Increases Cellular Permissiveness to Human Immunodeficiency Virus Replication and Reactivates Virus from Latency", *J. Virology*, 1995, 69(2), 1243–1252.

Levy et al., "Isolation of Lymphocytopathic Retroviruses from San Francisco Patients with AIDS", *Science*, 1984, 225, 840–842.

Levy et al., "Induction of Cell Differentiation by Human Immunodeficiency Virus 1 vpr", *Cell*, 1993, 72, 541–550.

Li, Gongrong et al., "Human Immunodeficiency Virus Type 1 DNA Synthesis, Integration, and Efficient Viral Replication in Growth–Arrested T Cells", *J.Virology*, 1993, 67, 3969–3977.

Ling et al., "Optimization of the Polymerase Chain Reaction with Regard to Fidelity: Modified t&, Taq, and Vent DNA Polymerases", *PCR Methods and Applications*, 1991, 1,63–69.

Macreadie, I. et al., "A Domain of Human Immunodeficiency Virus Type 1 Vpr Containing Repeated H(S/F)RIG Amino Acid Motifs Causes Cell Growth Arrest and Structural Defects", *PNAS USA*, 1995, 92, 2770–2774.

Morgenstern, J.P. et al., "Advanced mammalian gene transfer: high titre retroviral vectors with multiple drug selection markers and a complementary helper–free packaging cell line", *Nucl. Acids Res.*, 1990, 18, 3587–3596.

Myers, G. et al., "The Emergence of Simian/Human Immunodeficiency Virus", *Aids Research Human Retroviruses*, 1992, 8, 373–386.

Ogawa, K. et al., "Mutational analysis of the human immunodeficiency virus vpr open reading frame", *J. Virology*, 1989, 63(9), 4110–4114.

Ratner, L. et al., "Complete Nucleotide Sequence of the AIDS virus, HTLV–III", *Nature*, 1985, 313(1), 277–284.

Ratner, et al., "Complete Nucleotide Sequences of Functional Clones of the AIDS Virus", *Aids Research Human Retroviruses*, 1987, 3, 57–69.

Re, F. et al., "Human Immunodeficiency Virus Type 1 Vpr Arrests the Cell Cycle in $G_2$ by Inhibiting the Activation of $p34^{cdc2}$–Cyclin B", *J. Virology*, 1995, 69(11), 6859–6864.

Rafaeli, Y. et al., "Recombinant HIV–1 Vpr Protein Induces Cellular Differentiation in Vitro", *J. Cell. Biochem.*, Supplement 18B, 1994, Jan. 21–Feb. 13, 1994, Keystone Symposia on Molecular & Cellular Biology, p. 140, Abs. J 262.

Rafaeli, Y. et al., "The Glucocorticoid Receptor Type II Complex is a Target of the HIV–1 vpr Gene Product", *PNAS USA*, 1995, 92, 3621–3625.

Reiss et al., "Antibody response to viral proteins U (vpu) and R (vpr) in HIV–1–infected individuals", *Acquired Immune Deficiency Syndromes*, 1990, 3, 115–122.

Rich et al., Increased susceptibility of differentiated mononuclear phagocytes to productive infection with human immunodeficiency virus–1 (HIV–1), *American Society for Clinical Investigations, Inc.*, 1992, 89, 176–183.

Rogel, M. et al., "The Human Immunodeficiency Virus Type 1 vpr Gene Prevents Cell Proliferation During Chronci Infection", *J. Virology*, 1995 69(2), 882–888.

Rose et al., "Frequent identification of HIV–1 DNA in bronchoalveolar lavage cells obtained from individuals with the acquired immunodeficiency syndrome", *Am Rev Respir. Dis.*, 1991, 143, 850–854.

Roulston et al., "Induction of monocytic differentiation and NF–kB–like activities by human immunodeficiency virus 1 infection of Myelomonoblastic cells", *J. Exp. Med.*, 1992, 175, 751–763.

Salahuddin, Syed Z. et al., "Human T Lymphotropic Virus Type III Infection of Human Alveolar Macrophages", *Blood*, 1986, 68, 281–284.

Sato, A. et al., "Identification and Localization of vpr Gene Product of Human Immunodeficiency Virus Type 1", *Virus Genes*, 1990, 4(4), 303–312.

Schuitemaker, H. et al., "Biological Phenotype of Human Immunodeficiency Virus Type 1 Clones at Different Stages of Infection: Progression of Disease Is Associated with a Shift from Monocytotropic to T–Cell–Tropic Virus Populations",*J. Virology*, 1992, 66(3), 1354–1360.

Shibata, Riri et al., "Mutational Analysis of Simian Immunodeficiency Virus From African Green Monkeys and Human Immunodeficiency Virus Type 2" *J. Med. Primatol.*, 1990, 19, 217–225.

Shibata et al., "Mutational Analysis of the Human Immunodeficiency Virus Type 2 (HIV–2) Genome in Relation to HIV–1 and Simian Immunodeficiency Virus SIV $_{AGM}$", *J. Virology*, 1990, 64, 742–747.

Siegel and Lukas, "Morphological and Biochemical Differentiation of the Human Medulloblastoma Cell Line in TE671", *Dev. Brain Res.*, 1988, 44, 269–280.

Starcich et al., "Characterization of Long Terminal Repeat Sequences of HTLV–III", *Science*, 1985, vol. 227, 538–540.

Stratton et al., "Characterization of the human cell line TE671", *Carcinogenesis*, 1989, 10, 899–905.

Valentin, Antonio et al., "In Vitro Maturation of Mononuclear Phagocytes and Susceptibility to HIV–1 Infection", *Acquired Immune Deficiency Syndromes*, 1991, 4, 751–759.

Voller et al., eds., "Immunoassays for the 80's", University Park, 1981.

Weiner et al., "Linkage of tyrosine kinase activity with transforming ability of the p185neu oncoprotein", *Oncogene*, 1989, 4, 1175–1183.

Weiner et al., "Human genes other than CD4 facilitate HIV–1 infection of murine cells", *Pathobiology*, 1991, 59, 361–371.

Westervelt et al., "Dual regulation of silent and productive infection in monocytes by distinct human immunodeficiency virus type 1 determinants", *Virology*, 1992, 66(6), 3925–3931.

Wide, L., "Solid phase antigen–antibody systems", in *Radioimmunoassay Methods*, 1970, Churchill Livinstone, Edinburgh and London, 405–412.

Wong–Staal et al., "Human immunodeficiency virus: the eighth gene", *Aids Res. Human Retroviruses*, 1987, 3(1), 33–39.

Work, T.S. et al., "Laboratory Techniques and Biochemistry in Molecular Biology", North Holland Publishing Company, N.Y., 1978.

Yu, X. et al., "Open reading frame vpr of simian immunodeficiency virus encodes a virion–associated protein", *J. Virology*, 1990, 64(11), 5688–5693.

Yuan, w. et al., "Human immunodeficiency virus vpr gene encodes a virion–associated protein", *Aids Research Human Retroviruses*, 1990, 6(11), 1265–1271.

Zack, J.A. et al., "HIV–I production from infected peripheral blood T cells after HTLV–I induced mitogenic stimulation", *Science*, 1988, 240, 1026–1029.

Zhao, L. et al., "Biochemical mechanism of HIV–I Vpr function", *J. Biol. Chem.*, 1994, 269(22), 15577–15582.

USSN 08/019,601, filed Feb. 19, 1993 entitled "VPR Function and Activity".

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "oligonucleotide"

(xi) SEQUENCE DESCRIPTION: SEQ ID NO:1:

TGGATCCATG GAACAAGCCC AGAAGACCAA G                    31

(2) INFORMATION FOR SEQ ID NO:2:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "oligonucleotide"

(xi) SEQUENCE DESCRIPTION: SEQ ID NO:2:

ATGTCGACGC TATGTCGACA CCCAATTCTG AA                   32

(2) INFORMATION FOR SEQ ID NO:3:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "oligonucleotide"

(xi) SEQUENCE DESCRIPTION: SEQ ID NO:3:

TGGATCCATG GAACAAGCCC AGAAGACCAA G                    31

(2) INFORMATION FOR SEQ ID NO:4:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:4:

GGGGATCCTT AGGATCTCTG GCTCCATTTC T                                    31

(2) INFORMATION FOR SEQ ID NO:5:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:5:

TCATCGGAAG AGAGTAG                                                    17

(2) INFORMATION FOR SEQ ID NO:6:

(i) SEQUENCE CHARACTERISTICS:
            (A) LENGTH: 356 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO:6:

GAATTCGGCT TGTGAACTTG CGGGGTTTTT CAGTATCTAC GATTCATAGA TCTGGAATTC      60

GCGGCCGCGT CGACAGAGCA TTGGAGATCA GCTTCCGCTA AGATGCTAGC TTGGCCAAGT     120

CTGTTATGTT CACCTGAAAA AGTCTTAGCA GAGAATTTTT GGATTCCCAC CCAAAAGCCC     180

TCTCAGACAC TCAAATGTCT ATCTTCTCCA GTCTACAAAT TACATATTCC CACCCAGCAT     240

TACAGATCTC GAACATGTTA TTTCTCCACT CACTGGTTTA AGTTGGGTTT AGCCACTGGA     300

TAAGTATTAT AATAGAGCTA CTTAGCTGTG GGTTTAATAC CCCTTCTTGT TAACAA        356

(2) INFORMATION FOR SEQ ID NO:7:

(i) SEQUENCE CHARACTERISTICS:
            (A) LENGTH: 342 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO:7:

GAATTCGGCT TACTTGCGGG GTTTTTCAGT ATCTACGATT CATAGATCTG GAATTCGCGG      60

CCGCGTCGAC TTTTTTTTTT TTTTTTTGGT ACAAGTAAAG TAGTATAATC CAAATTTATT     120

ATATCTAAGA GGCTATCATG GGCTGTAAGT AGAATCAAAG GTTAAGAACA TTTTATGCAC     180

TTATTCCACA AACATTTACT GAGCATACTA GGTGCTGGGA ATGTGACAGT GAGCAAAAAA     240

CACAAGAGTG TGCAAAGAGT GATCAAAATG TCAACCAGTA AGAACAGGGA AAGAGCTGTT     300

GAGGCCAAGA GGAGACGACT TAGTTCTAAA GTTTTTTGGA TT                       342

(2) INFORMATION FOR SEQ ID NO:8:

(i) SEQUENCE CHARACTERISTICS:
            (A) LENGTH: 374 base pairs (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:8:

GAATTCGGCT TGTGAACTTG CGGGGTTTTT CAGTATCTAC GATTCATAGA TCTGGAATTC      60

GCGGCGCGTC GACAGAGCAT TGGAGATCAG CTTCCGCTAA GATGCTAGCT TGGCCAAGTC     120

TGTTATGTTC ACCTGAAAAA GTCTTAGCAG AGAATTTTGG ATTCCCACCC AAAAGCCCTC     180

TCAGCACTCA AATGCCTATC TTCTCCAGTC TACAAGTTAC ATGTTCCCAC CCAGCATTAC     240

AGTCTTGAAC ATGTTATTTC TCCACTTACT GGTTTAAGTT GGGGTTTAGC ACTGGATAAG     300

TATTATATAG AGCTACTTAG CTGTGGGTTT AATACCCTCC TCTTAACAAT TGGAGGAAAT     360

TAATGGCTTT TTTA                                                      374

NUCLEOTIDE SEQUENCES ENCODING VPR RECEPTOR PROTEIN

CROSS REFERENCE TO RELATED APPLICATIONS

This application is a continuation of application Ser. No. 08/593,695 filed Jan. 29, 1996, now abandoned.

FIELD OF THE INVENTION

The present invention relates to a nucleic acid molecule that encodes a human receptor protein which binds to the human immunodeficiency virus (HIV) viral protein R (vpr), to pharmaceutical compositions that comprise the nucleic acid molecules, to compositions useful for and methods of making and using the receptor protein and the nucleic acid molecules that encode it.

BACKGROUND OF THE INVENTION

Since the demonstration in 1987 that the small open reading frame within HIV-1 designated R encodes a 15 kd protein (Wong-Staal, F., et al., (1987) *AIDS Res. Hum. Retroviruses* 3:33–39), relatively little regarding the function of the viral protein R (vpr) has been reported. The vpr open reading frame is conserved within all genomes of HIV-1 and HIV-2 and within most, if not all, simian immunodeficiency virus (SIV) genomes. VPR is immunogenic in vivo in that a large subset of HIV$^+$ individuals makes antibodies that can react with a bacterially produced vpr peptide (Wong-Staal, F., et al., (1987) *AIDS Res. Hum. Retroviruses* 3:33–39).

The progression from HIV infection to AIDS is in large part determined by the effects of HIV on the cells that it infects, including CD4$^+$ T lymphocytes and macrophages. On the other hand, cell activation, differentiation and proliferation are in turn thought to regulate HIV infection and replication in T cells and macrophages. Gallo, R. C. et al. (1984) *Science* 224:500; Levy, J. A. et al., (1984) *Science* 225:840; Zack, J. A. et al. (1988) *Science* 240:1026; Griffin, G. E. et al., (1988) *Nature* 339:70; Valentin, A. et al. (1991) *J. AIDS* 4:751; Rich, E. A. et al., (1992) *J. Clin. Invest.* 89:176; and Schuitemaker, H. et al. (1992) *J. Virol.* 66:1354. Cell division per se may not be required since HIV and other lentiviruses can proliferate in nonproliferating, terminally differentiated macrophages and growth-arrested T lymphocytes. Rose, R. M. et al. (1986) *Am. Rev. Respir. Dis.* 143:850; Salahuddin, S. Z. et al. (1986) *Blood* 68:281; and Li, G. et al. (1993) *J. Virol.* 67:3969. The ability of lentiviruses, including HIV, to replicate in nonproliferating cells, particularly in macrophages, is believed to be unique among retroviruses and it may be significant that several lentiviruses contain a vpr-like gene. Myers, G. et al. (1992) *AIDS Res. Hum. Retrovir.* 8:373. HIV infection of myeloid cell lines can result in a more differentiated phenotype and increase the expression of factors such as NF-KB which are necessary for HIV replication. Roulston, A. et al. (1992) *J. Exp. Med.* 175:751; and Chantal Petit, A. J. et al. (1987) *J. Clin. Invest.* 79:1883.

The most evidence for the function of the vpr protein comes from several studies reporting the activities of HIV strains that have mutations in the vpr gene. It has been reported that mutations in the vpr gene result in a decrease in the replication and cytopathogenicity of HIV-1, HIV-2, and SIV in primary CD4$^+$ T lymphocytes and transformed T cell lines (Ogawa, K., et al., (1989) *J. Virol.* 63:4110–4114; Shibata, R., et al. (1990a). *J. Med. Primatol.* 19:217–225; Shibata, R., et al. (1990b) *J. Virol.* 64:742–747 and Westervelt, P. et al. (1992) *J. Virol.* 66:3925), although others have reported mutated vpr gene had no effect on replication (Dedera, D., et al. (1989) *Virol.* 63:3205–3208). Interestingly HIV-2 mutated for vpr has been reported unable to infect primary monocyte/macrophages (Hattori, N., et al. (1990) *Proc. Natl. Acad. Sci. USA* 87:8080–8084). Transactivation of the HIV long terminal repeat and heterologous promoters by HIV is increased about 3-fold in wild-type versus vpr-negative HIV-1, though the mechanism through which vpr may transactivate transcription is unknown and may be indirect (Cohen, E. A., et al., (1990b) *J. Acquir. Immune Defic. Syndr.* 3:11–18). The relationship between the effects of vpr on promoter activity and viral infectivity is not clear. Vpr protein is incorporated into the viral particle, and this finding has led to the proposition that vpr functions early in infection, following virus penetration and uncoating, and that vpr may interact with cellular regulatory mechanisms important in the establishment of infection (Cohen, E. A., et al. 1990a *J. Virol.* 64:3097–3099; Yu, X. F., et al. (1990) *J. Virol.* 64:5688–5693.; and, Yuan, X., et al., (1990) *AIDS Res. Hum. Retroviruses* 6:1265–1271).

The vpr gene of HIV-1 has been shown to induce cellular growth inhibition and differentiation in tumor lines of intermediate differentiation in vitro. Levy, D. N. et al. (1993) *Cell* 72:541. Since vpr protein originates within viral particles, vpr may play a role in establishing productive infection.

There is a need to understand the activity of vpr and its role in HIV infection at the molecular and cellular level. There is a need to identify the cellular proteins that bind to vpr. There is a need to identify molecules that inhibit vpr activity. There is a need for anti-HIV therapeutics and protective agents.

SUMMARY OF THE INVENTION

The present invention relates to nucleic acid molecules that encode rip-1, a human protein that occurs in the cytoplasm of human cells, binds to vpr, and is transported from the cytoplasm to the nucleus when bound to vpr; or a fragment thereof.

The present invention relates to an expression vector that comprises a nucleotide sequence that encodes rip-1, or a nucleic acid molecule that comprises a nucleotide sequence that encodes a fragment thereof.

The present invention relates to a host cell which comprises an expression vector that comprises a nucleotide sequence that encodes rip-1, or a nucleic acid molecule that comprises a nucleotide sequence that encodes a fragment thereof.

The present invention relates to a method of producing rip-1 protein or a fragment thereof comprising the step of culturing a host cell that comprises an expression vector that comprises a nucleotide sequence that encodes rip-1 or a fragment thereof and isolating the protein of fragment that is produced in the cultured cells.

The present invention relates to probes and methods for identifying nucleic acid molecules that encode rip-1.

The present invention relates to essentially pure human protein that has an apparent molecular weight of between 40–43 kD, that occurs in the cytoplasm of human cells, that binds to vpr and that is transported from the cytoplasm to the nucleus when bound to vpr; or a fragment thereof.

The present invention relates to a nucleic acid molecule that comprises a nucleotide sequence that encodes the human protein that has an apparent molecular weight of between 40–43 kD, that occurs in the cytoplasm of human cells, that binds to vpr and that is transported from the cytoplasm to the nucleus when bound to vpr or a nucleic acid molecule that comprises a nucleotide sequence that encodes a fragment thereof.

The present invention relates to an expression vector that comprises a nucleotide sequence that encodes the human protein that has an apparent molecular weight of between 40–43 kD, that occurs in the cytoplasm of human cells, that binds to vpr and that is transported from the cytoplasm to the nucleus when bound to vpr or a nucleic acid molecule that comprises a nucleotide sequence that encodes a fragment thereof.

The present invention relates to a host cell which comprises an expression vector that comprises a nucleotide sequence that encodes the human protein that has an apparent molecular weight of between 40–43 kD, that occurs in the cytoplasm of human cells, that binds to vpr and that is transported from the cytoplasm to the nucleus when bound to vpr or a nucleic acid molecule that comprises a nucleotide sequence that encodes a fragment thereof.

The present invention relates to a method of producing a human protein that has an apparent molecular weight of between 40–43 kD, that occurs in the cytoplasm of human cells, that binds to vpr and that is transported from the cytoplasm to the nucleus when bound to vpr or a nucleic acid molecule that comprises a nucleotide sequence that encodes a fragment thereof comprising the step of culturing a host cell that comprises an expression vector that comprises a nucleotide sequence that encodes the human protein that has an apparent molecular weight of between 40–43 kD, that occurs in the cytoplasm of human cells, that binds to vpr and that is transported from the cytoplasm to the nucleus when bound to vpr or a nucleic acid molecule that comprises a nucleotide sequence that encodes a fragment thereof and isolating the protein of fragment that is produced in the cultured cells.

The present invention relates to a method of identifying compounds which inhibit vpr protein binding to the human protein that has an apparent molecular weight of between 40–43 kD, that occurs in the cytoplasm of human cells, that binds to vpr and that is transported from the cytoplasm to the nucleus when bound to vpr that comprises the steps of contacting vpr protein and the human protein that has an apparent molecular weight of between 40–43 kD, that occurs in the cytoplasm of human cells, that binds to vpr and that is transported from the cytoplasm to the nucleus when bound to vpr or a fragment thereof in the presence of a test compound, determining the level of binding and comparing that level to the level of binding that occurs when vpr protein and the human protein that has an apparent molecular weight of between 40–43 kD, that occurs in the cytoplasm of human cells, that binds to vpr and that is transported from the cytoplasm to the nucleus when bound to vpr are contacted in the absence of a test compound.

The present invention relates to a kit for identifying compounds which inhibit vpr protein binding to the human protein that has an apparent molecular weight of between 40–43 kD, that occurs in the cytoplasm of human cells, that binds to vpr and that is transported from the cytoplasm to the nucleus when bound to vpr which comprises a first container comprising vpr protein and a second container comprising the human protein that has an apparent molecular weight of between 40–43 kD, that occurs in the cytoplasm of human cells, that binds to vpr and that is transported from the cytoplasm to the nucleus when bound to vpr or a fragment thereof.

The present invention relates to antibodies that specifically bind to the human protein that has an apparent molecular weight of between 40–43 kD, that occurs in the cytoplasm of human cells, that binds to vpr and that is transported from the cytoplasm to the nucleus when bound to vpr.

The present invention relates to pharmaceutical compositions that comprise the human protein that has an apparent molecular weight of between 40–43 kD, that occurs in the cytoplasm of human cells, that binds to vpr and that is transported from the cytoplasm to the nucleus when bound to vpr or a fragment thereof and a pharmaceutically acceptable carrier.

The present invention relates to a method of treating an individual exposed to HIV by administering the human protein that has an apparent molecular weight of between 40–43 kD, that occurs in the cytoplasm of human cells, that binds to vpr and that is transported from the cytoplasm to the nucleus when bound to vpr.

DESCRIPTION OF PREFERRED EMBODIMENTS OF THE INVENTION

The present invention arises out of the discovery that HIV regulatory protein vpr (referred to herein as "vpr protein") binds to a human protein that has an apparent molecular weight of between 40–43 kD, that occurs in the cytoplasm of human cells. It has been discovered that when vpr binds to the human protein that has an apparent molecular weight of between 40–43 kD, that occurs in the cytoplasm of human cells, the proteins are transported from the cytoplasm to the nucleus.

As used herein, the term "vpr receptor protein" is meant to refer to the human protein that has an apparent molecular weight of between 40–43 kD, that occurs in the cytoplasm of human cells, that binds to vpr and that is transported from the cytoplasm to the nucleus when bound to vpr. The vpr receptor protein is colocalized with the T-cell and B-cell transcription factor NFκB. As described in U.S. patent application Ser. No. 08/019,601 filed Feb. 19, 1993 entitled VPR Function and Activity and the U.S. patent application filed herewith which is entitled VPR Function and Activity and which is a continuation in part of U.S. patent application Ser. No. 08/019,601, both of which are incorporated herein by reference, vpr has several activities which are involved in HIV infection. In particular, vpr is believed to enhance retroviral infection by causing changes in cells that make them better hosts for HIV replication.

The discovery of the vpr receptor protein in human cells and its transport from cytoplasm to the nucleus when bound to vpr indicate that the binding of vpr to the human receptor protein is involved in HIV replication and thus pathogenesis. Accordingly, the inhibition of such interaction effectively inactivates vpr and prevents it from converting cells to better HIV replication hosts.

The present invention relates to essentially pure human vpr receptor protein. The vpr receptor protein has an apparent molecular weight of between 40–43 kD, that occurs in the cytoplasm of human cells, that binds to vpr and that is transported from the cytoplasm to the nucleus when bound to vpr; or a fragment thereof. The vpr receptor protein can be isolated from human cells by passing a human cell preparation through an immobilized vpr column under conditions which allow vpr/vpr receptor binding and then changing the conditions to those which do not favor such binding. The released vpr receptor can be collected in essentially pure form. Further purification may be achieved using routine chromatography means.

The following procedure may be used to purify vpr receptor proteins. Cell extracts from primary T cells and monocytes as well as peripheral blood cells and macrophages are obtained by methods known to those skilled in the art. Cell extracts are separated by affinity chromatography. Briefly, eukaryotically-produced vpr is immobilized to a solid support matrix via one or more covalent bonds. Solid support matrices include agarose, polyacrylamide-agarose, controlled-pore glass and other such materials known to those skilled in the art. One skilled in the art will readily appreciate the standard techniques involved in coupling vpr to the matrix as well as techniques involved in activation of the matrix. A spacer molecule may be employed to distance vpr from the matrix backbone in order to allow vpr to more freely bind proteins in the cell extract. One skilled in the art will readily appreciate the variety of spacer molecules with which to use.

The cell extract is layered onto the vpr affinity column by standard methods known to those skilled in the art. Appropriate buffers, washing conditions and elution conditions, which are known to those skilled in the art, are chosen. The resulting eluate may be further purified to homogeneity by techniques such high performance liquid chromatography (HPLC) or other such methods as known to those skilled in the art.

The vpr receptor protein has been purified to approximately 95% purity by a vpr-affinity column using this technique of purification. Said protein has a molecular weight of about 40–43 kDa when separated by reducing SDS-PAGE. The protein has been detected in rhabdomyosarcoma cell lines TE 671 and RD; osteosarcoma cell lines D17 and HOS; gliablastoma cell lines HTB14, U373 and HBT10; as well as T-cell lines Supt-1 and H9 and monocyte/macrophage lines U937, THP-1, KG-1 and HL-60 as well as primary cells.

The present invention relates to nucleic acid molecules that comprise a nucleotide sequence that encodes rip-1. The nucleic acid molecule can be incorporated into a plasmid vector or any other vector capable of expressing rip-1. In addition, mammalian cells as well as bacterial cells may be transformed with the plasmid construct containing the sequence, or derivatives thereof, encoding rip-1 protein. Said transformed cells may produce rip-1 protein intracellularly or extracellularly.

In addition, oligonucleotides corresponding to the portions of the sense or antisense of rip-1 DNA, including gDNA, or mRNA may also be produced. These oligonucleotides may comprise between 10 and 5000 nucleotides, preferably between 10 and 500 nucleotides, most preferably between 10 and 100 nucleotides. Such nucleic acid molecules may be used to suppress gene expression or to probe nucleic acid libraries and Southern blots to identify nucleic acid molecules that encode rip-1.

DNA molecules comprising one or more of the sequences shown in SEQ ID NO:6, SEQ ID NO:7, and SEQ ID NO:8 can be used as probes to identify clones that encode the rip-1 protein. DNA molecules comprising one or more of the sequences shown in SEQ ID NO:6, SEQ ID NO:7, and SEQ ID NO:8 may consist of up to about 4000 bases, preferably about 10–1000, more preferably about 50–1000. In some embodiments, the DNA molecules consist of 100–1000. These DNA molecules, which are up to 4000 bases and which comprise SEQ ID NO:6 and/or SEQ ID NO:7 and/or SEQ ID NO:8, may be used as inserts which are inserted into vectors including expression vectors useful to express such sequences and produce translation products therefrom. Such translation products are useful to produce antibodies that bind to rip-1. When used as probes, it is preferred that SEQ ID NO:6 and/or SEQ ID NO:7 and/or SEQ ID NO:8 and/or SEQ ID NO:9 constitutes at least 30%, preferably 50% and most preferably 75%+ of the total DNA molecule.

The present invention relates to an expression vector that comprises a nucleotide sequence that encodes rip-1.

The present invention relates to a host cell which comprises an expression vector that comprises an expression vector that comprises a nucleotide sequence that encodes rip-1.

The present invention relates to a method of producing rip-1 protein or a fragment thereof comprising the step of culturing a host cell that comprises an expression vector that comprises a nucleotide sequence that encodes the rip-1 protein.

Rip-1 protein may be produced by routine means using readily available starting materials as described above. Provision of a suitable DNA sequence encoding the desired protein permits the production of the protein using recombinant techniques now known in the art. The DNA sequence may also be obtained from human cells as gDNA or cDNA, or can be prepared chemically using a synthesized nucleotide sequence. When the coding DNA is prepared synthetically, advantage can be taken of known codon preferences of the intended host where the DNA is to be expressed.

One having ordinary skill in the art can, using well known techniques, obtain a DNA molecule encoding rip-1 protein and insert that DNA molecule into a commercially available expression vector for use in well known expression systems. For example, the commercially available plasmid pSE420 (Invitrogen, San Diego, Calif.) may be used for production in *E. coli*. The commercially available plasmid pYES2 (Invitrogen, San Diego, Calif.) may be used for production in *S. cerevisiae* strains of yeast. The commercially available MaxBac™ (Invitrogen, San Diego, Calif.) complete baculovirus expression system may be used for production in insect cells. The commercially available plasmid pcDNA I (Invitrogen, San Diego, Calif.) may be used for production in mammalian cells such as Chinese Hamster Ovary cells. One having ordinary skill in the art can use these commercial expression vectors systems or others to produce vpr receptor protein using routine techniques and readily available starting materials.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989).

Thus, the desired proteins can be prepared in both prokaryotic and eukaryotic systems, resulting in a spectrum of processed forms of the protein.

The most commonly used prokaryotic system remains *E. coli*, although other systems such as *B. subtilis* and Pseudomonas are also useful. Suitable control sequences for prokaryotic systems include both constitutive and inducible promoters including the lac promoter, the trp promoter, hybrid promoters such as tac promoter, and the lambda phage Pl promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in prokaryotic hosts in this matter, the signal sequence is removed upon secretion.

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but are not limited to, yeast, fungal cells, insect cells, mammalian cells, avian cells, and cells of higher plants. Suitable promoters are available which are compatible and operable for use in each of these host types as well as are termination sequences and enhancers, as e.g. the baculovirus polyhedron promoter. As above, promoters can be either constitutive or inducible. For example, in mammalian systems, the mouse metallothionene promoter can be induced by the addition of heavy metal ions.

The particulars for the construction of expression systems suitable for desired hosts are known to those in the art. For recombinant production of the protein, the DNA encoding it is suitably ligated into the expression vector of choice and then used to transform the compatible host which is then cultured and maintained under conditions wherein expression of the foreign gene takes place. The protein of the present invention thus produced is recovered from the culture, either by lysing the cells or from the culture medium as appropriate and known to those in the art.

One having ordinary skill in the art can, using well known techniques, isolate rip-1 protein or fragments thereof produced using such expression systems.

In addition to isolating vpr receptor protein from natural sources and producing vpr receptor protein or fragments thereof by recombinant techniques, automated amino acid synthesizers may also be employed to produce vpr receptor protein or fragments thereof. It should be further noted that if the proteins herein are made synthetically, substitution by amino acids which are not encoded by the gene may also be made. Alternative residues include, for example, the ω amino acids of the formula $H_2N(CH_2)_nCOOH$ wherein n is 2–6. These are neutral, nonpolar amino acids, as are sarcosine (Sar), t-butylalanine (t-BuAla), t-butylglycine (t-BuGly), N-methyl isoleucine (N-MeIle), and norleucine (Nleu). Phenylglycine, for example, can be substituted for Trp, Tyr or Phe, an aromatic neutral amino acid; citrulline (Cit) and methionine sulfoxide (MSO) are polar but neutral, cyclohexyl alanine (Cha) is neutral and nonpolar, cysteic acid (Cya) is acidic, and ornithine (Orn) is basic. The conformation conferring properties of the proline residues may be obtained if one or more of these is substituted by hydroxyproline (Hyp).

The pharmaceutical composition comprising vpr receptor protein or a fragment thereof and a pharmaceutically acceptable carrier or diluent may be formulated by one having ordinary skill in the art with compositions selected depending upon the chosen mode of administration. Suitable pharmaceutical carriers are described in the most recent edition of *Remington's Pharmaceutical Sciences*, A. Osol, a standard reference text in this field.

For parenteral administration, the vpr receptor protein or a fragment thereof can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions according to the present invention may be administered as a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The pharmaceutical compositions comprising vpr receptor protein, or fragments or derivatives may be administered by any means that enables the active agent to reach the agent's site of action in the body of a mammal. The dosage administered varies depending upon factors such as: pharmacodynamic characteristics; its mode and route of administration; age, health, and weight of the recipient; nature and extent of symptoms; kind of concurrent treatment; and frequency of treatment. Usually, a daily dosage of vpr receptor protein can be about 1 μg to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Another aspect of the present invention relates to pharmaceutical compositions that comprise a nucleic acid molecule that encodes vpr receptor protein or a fragment thereof and a pharmaceutically acceptable carrier or diluent. According to the present invention, genetic material that encodes vpr receptor protein or a fragment thereof is delivered to an individual in an expressible form. The genetic material, DNA or RNA, is taken up by the cells of the individual and expressed. Pharmaceutical compositions comprising genetic material that encodes vpr receptor protein are useful in the same manner as pharmaceutical compositions comprising vpr receptor protein.

The pharmaceutical compositions according to this aspect of the present invention comprise about 0.1 to about 1000 micrograms of DNA. In some preferred embodiments, the pharmaceutical compositions contain about 1 to about 500 micrograms of DNA. In some preferred embodiments, the pharmaceutical compositions contain about 25 to about 250 micrograms of DNA. Most preferably, the pharmaceutical compositions contain about 100 micrograms DNA.

The pharmaceutical compositions according to this aspect of the present invention are formulated according to the mode of administration to be used. One having ordinary skill in the art can readily formulate a nucleic acid molecule that encodes vpr receptor protein. In cases where intramuscular injection is the chosen mode of administration, an isotonic formulation is used. Generally, additives for isotonicity can include sodium chloride, dextrose, mannitol, sorbitol and lactose. Isotonic solutions such as phosphate buffered saline may be used. Stabilizers include gelatin and albumin.

The present invention relates to a method of treating an individual exposed to HIV by administering pharmaceutical compositions that comprise the vpr receptor protein or fragments thereof. Fragments which bind to vpr are particularly useful.

Another aspect of the invention relates to methods of identifying compounds which inhibit vpr protein binding to vpr receptor protein. The methods comprise the steps of first contacting, in the presence of a test compound, vpr protein and vpr receptor protein and then determining the level of binding. Compounds which interfere with the binding of vpr to vpr receptor protein are useful to impede HIV replication; therefore such compounds will be useful as anti-HIV therapeutics alone or as part of a multi-faceted anti-HIV drug regimen which includes other therapeutics.

To practice these aspects of the invention, vpr protein and vpr receptor protein are contacted in the presence of a test compound. The level of binding of the proteins is determined. The resultant level of binding is compared to the known level of binding that occurs when both proteins are contacted with each other. In the absence of a compound that interferes with the binding, the two proteins will bind. As a control, vpr protein and vpr receptor protein are contacted in the absence of a test compound.

Test compound is provided, preferably in solution. Serial dilutions of test compounds may be used in a series of assays. Test compound may be added at concentrations from 0.01 $\mu$M to 1M. A preferred range of final concentrations of a test compound is from 10 $\mu$M to 100 $\mu$M.

Production of vpr protein is described in the U.S. patent applications cited above which have been incorporated by reference. A preferred concentration range of the vpr used is about 1 $\mu$g/ml to 1 mg/ml. A preferred concentration of the vpr is about 50 $\mu$g/ml.

The vpr receptor protein may be produced by routine means using readily available starting materials following the teachings described herein. A preferred concentration range of the vpr receptor protein used is about 1 $\mu$g/ml to 1 mg/ml. A preferred concentration of the vpr receptor protein is about 50 $\mu$g/ml.

The means to detect whether or not vpr and vpr receptor protein are bound or if binding has been inhibited are routine and include enzyme assays and ELISA assays. One having ordinary skill in the art can detect protein binding using well known methods. One having ordinary skill in the art can readily appreciate the multitude of ways to practice a binding assay to detect compounds which modulate the binding of vpr to vpr receptor protein. For example, antibodies are useful for immunoassays which detect or quantitate vpr protein binding to vpr receptor protein. The immunoassay typically comprises incubating vpr protein and vpr receptor protein to allow protein-protein binding in the presence of a detectably labeled high affinity antibody capable of selectively binding to either vpr protein or vpr receptor protein, and detecting the labeled antibody which is bound to the protein. Various immunoassay procedures are described in *Immunoassays for the 80's*, A. Voller et al., Eds., University Park, 1981.

In this aspect of the invention, the antibody or either vpr protein or vpr receptor protein may be added to nitrocellulose, or other solid support which is capable of immobilizing proteins. The support may then be washed with suitable buffers followed by treatment with the detectably labeled vpr-specific antibody or the antibody that binds to the vpr receptor protein. The solid phase support may then be washed with the buffer a second time to remove unbound antibody. The amount of bound label on said solid support may then be detected by conventional means.

By "solid phase support" or "carrier" is intended any support capable of binding antigen or antibodies. Well-known supports or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support configuration may be spherical, as in a bead, or cylindrical, as in the inside surface of a test tube, or the external surface of a rod. Alternatively, the surface may be flat such as a sheet, test strip, etc. Those skilled in the art will know many other suitable carriers for binding antibody or antigen, or will be able to ascertain the same by use of routine experimentation.

The binding activity of a given lot of antibodies may be determined according to well known methods. Those skilled in the art will be able to determine operative and optimal assay conditions for each determination by employing routine experimentation.

Positive control assays may be performed in which no test compound is added.

One of the ways in which the antibodies can be detectably labeled is by linking the same to an enzyme and use in an enzyme immunoassay (EIA), or enzyme-linked immunosorbent assay (ELISA). This enzyme, when subsequently exposed to its substrate, will react with the substrate generating a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

By radioactively labeling the antibody, it is possible to detect it through the use of a radioimmunoassay (RIA) (see, for example, Work, T. S., et al., *Laboratory Techniques and Biochemistry in Molecular Biology*, North Holland Publishing Company, N.Y., 1978. The radioactive isotope can be detected by such means as the use of a gamma counter or a scintillation counter or by autoradiography. Isotopes which are particularly useful for the purpose of the present invention are: $^{3}H$, $^{125}I$, $^{131}I$, $^{35}S$, $^{14}C$, and, preferably, $^{125}I$.

It is also possible to label the antibody with a fluorescent compound. When the fluorescent labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence-emitting metals such as $^{152}Eu$, or others of the lanthanide series. These metals can be attached to the TNF-specific antibody using such metal chelating groups as diethylenetriaminepentaacetic acid (DTPA) or ethylenediaminetetraacetic acid (EDTA).

The antibody also can be detectably labeled by coupling to a chemiluminescent compound. The presence of the chemiluminescently labeled antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin. Detection of the vpr-specific antibody or the antibody that binds to the vpr receptor protein may be accomplished by a scintillation counter, for example, if the detectable label is a radioactive gamma emitter, or by a fluorometer, for example, if the label is a fluorescent material.

In the case of an enzyme label, the detection can be accomplished by colorometric methods which employ a substrate for the enzyme. Detection may also be accomplished by visual comparison of the extent of enzymatic reaction of a substrate in comparison with similarly prepared standards.

As can be readily appreciated, one of the viral proteins may also be detectable and serve as a reporter molecule instead of or in addition to the antibody.

The components of the assay may be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested and a quantity of detectably labeled soluble antibody is added to permit detection and/or quantitation of the ternary complex formed between solid-phase antibody, antigen, and labeled antibody.

Typical and preferred immunometric assays include "forward" assays in which the antibody bound to the solid phase is first contacted with the one of the viral proteins to immobilize it. The second viral protein is added in the presence of the test compound. After a suitable incubation period, the solid support is washed to remove unbound protein. A second antibody is then added which is specific for the second viral protein. The second antibody is preferably detectable. After a second incubation period to permit the labeled antibody to complex with the second viral protein bound to the solid support through the unlabeled antibody and first viral protein, the solid support is washed a second time to remove the unreacted labeled antibody. This type of forward sandwich assay may be a simple "yes/no" assay to determine whether binding has occurred or may be made quantitative by comparing the measure of labeled antibody with that obtained in a control. Such "two-site" or "sandwich" assays are described by Wide, *Radioimmune Assay Method*, Kirkham, Ed., E. & S. Livingstone, Edinburgh, 1970, pp. 199–206).

Other type of "sandwich" assays are the so-called "simultaneous" and "reverse" assays. A simultaneous assay involves a single incubation step wherein the antibody bound to the solid support and labeled antibody, both viral protein and the test compound are added at the same time. After the incubation is completed, the solid support is washed to remove uncomplexed proteins. The presence of labeled antibody associated with the solid support is then determined as it would be in a conventional "forward" sandwich assay.

In the "reverse" assay, stepwise addition first of a solution of labeled antibody to the viral proteins followed by the addition of unlabeled antibody bound to a solid support after a suitable incubation period, is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays. In one embodiment, a combination of antibodies of the present invention specific for separate epitopes may be used to construct a sensitive three-site immunoradiometric assay.

In some preferred embodiments, an anti-vpr antibody is fixed to a solid phase. vpr protein is contacted with the fixed antibody to form a complex. The complex is contacted with a vpr receptor protein in the presence of a test compound. Antibodies that bind to the vpr receptor protein are then added. The solid phase is washed to remove unbound material. A control assay is performed in an identical manner except that no test compound is used. Detection of the antibodies that bind to the vpr receptor protein indicates that the vpr and vpr receptor proteins are capable of binding to each other in the presence of the test compound. Accordingly, failure to detect that antibodies that bind to vpr protein indicates that the test compound inhibits binding of vpr and vpr receptor proteins. Quantifying the level of binding in the presence and absence of test compound allows for the measurement of the extent of modulation that the test compound can cause on vpr binding to vpr receptor protein.

In some preferred embodiments, antibodies that bind to the vpr receptor protein are fixed to a solid phase. vpr receptor protein is contacted with the fixed antibody to form a complex. The complex is contacted with vpr protein in the presence of a test compound. Anti-vpr antibodies are then added. The solid phase is washed to removed unbound material. A control assay is performed in an identical manner except that no test compound is used. Detection of the antibodies that bind to vpr protein indicates that the vpr and vpr receptor proteins are capable of binding to each other in the presence of the test compound. Accordingly, failure to detect that antibodies that bind to vpr protein indicates that the test compound inhibits binding of vpr and vpr receptor proteins. Quantifying the level of binding in the presence and absence of test compound allows for the measurement of the extent of modulation that the test compound can cause on vpr binding to vpr receptor protein.

In the methods of identifying compounds that inhibit vpr protein binding to vpr receptor protein, fragments of vpr may be used provided the fragment used retains its ability to bind to the vpr receptor protein. Similarly, fragments of vpr receptor protein may be used provided the fragment used retains its ability to bind to vpr protein.

A further aspect of the present invention relates to kits for practicing the above described method of identifying compounds which inhibit vpr protein binding to vpr receptor protein. Kits according to this aspect of the invention comprise a first container comprising vpr protein, a second container comprising vpr receptor protein. Additionally, to practice the above defined method, means are required to distinguish vpr protein bound to the vpr receptor protein from unbound vpr protein or unbound vpr receptor protein. In a preferred embodiment of this aspect of the invention, a third container comprising an antibody that specifically binds to either the vpr protein or vpr receptor protein is provided. At least one of the contained components, preferably the antibody, may be conjugated with an agent, such as those described above, which allows its presence to be detected. In another preferred embodiment of this aspect of the invention, a fourth container is provided which contains an antibody that specifically binds to either the vpr protein or vpr receptor protein, but not the protein which is bound by the antibody in the third container. At least one of the contained components, preferably the antibody, may be conjugated with an agent, such as those described above, which allows its presence to be detected. In the kits of the invention which are useful to practice the methods of identifying compounds that inhibit vpr protein binding to a protein, fragments of vpr may be included provided the fragment used retains its ability to bind to the vpr receptor protein. Similarly, fragments of vpr receptor protein may be included provided the fragment used retains its ability to bind to vpr protein.

The present invention relates to antibodies that specifically bind to the human protein that has an apparent molecular weight of between 40–43 kD, that occurs in the cytoplasm of human cells, that binds to vpr and that is transported from the cytoplasm to the nucleus when bound to vpr. Production of such antibodies can be achieved by those having ordinary skill in the art without undue experimentation using readily available starting materials. The antibodies are useful in the assay to identify compounds that inhibit vpr binding to vpr receptor protein.

EXAMPLES

Example 1

Supernatants that contained vpr protein from insect cells infected with recombinant baculovirus that comprised a nucleotide sequence that encodes vpr were passed over a column. The column was washed with PBS. Cell lysates from U937 cells lysed in 100 mM NaCl, 50 mM Tris pH 8.0, 0.5% triton X-100 were then passed over the vpr loaded column and washed with PBS. The column was eluted with 100 mM triethanolamine, pH 11.5. The eluate was neutralized with 1M sodium phosphate, pH 6.8. Vpr and vpr receptor protein were coeluted as concluded from ELISA, SDS PAGE, silver stain or western blot.

vpr receptor protein was further purified by adding rabbit anti-vpr coated beads to the eluate. The beads are covalently bound to the antibody and the elution is done with the same triethanolamine solution described above. The beads are washed with PBS and eluted. The eluate is supplemented with equimolar amounts of gag p24. This solution is incubated at room temperature for 30 minutes. After incubation, beads coupled to a different anti-vpr antibody as well as antibody V7.8 are added to the solution. The supernatant is collected and contains greater than 90% pure vpr receptor protein which can be further purified by chromatography.

Example 2

Peptides that consist of vpr residues 27–39, 35–48, 41–55, 49–60 and 66–68 inhibit vpr/vpr receptor binding. Anti-vpr antibody that binds to vpr peptide 41–60 inhibit vpr/vpr receptor binding.

Example 3

In identifying Rip-1, the results of co-immunoprecipitation assays yielded proteins of differing sizes. Cytosolic Rip-1 was identified as a 41-kDa size with additional proteins of 34 kd and 18 kd (Refaeli, Y., et al. (1995) *Proc. Nat. Acad. Sci., USA* 92:3621–3625). The protein has also been precipitated as a 180-kDa cellular protein (Zhao, L. J., et al. (1994) *J. Biol. Chem.* 269 December 23, 32131–32137).

The fact that the identify of Rip-1 has yet to be conclusively determined means that the actual functions of this protein are under investigation. Current hypothesis support that Rip-1 is associated with the nuclear localization of Vpr and the possibility that the protein may be one of the regulatory proteins that are involved in the G2-M phase transition of the cell cycle and that Vpr is related to the GR pathway.

Using a yeast system (Fields, S. (1993) *Methods* 5:116–124; Fields, S. and Song, O. (1989) *Nature* 340:245–246; and, Fields, S. and Sternglanz, R. (1994) *Trends in Genetics* 10:286–292, which are each incorporated herein by reference) instead of the usual biochemical techniques such as cross linking, co-immunoprecipitation, and co-fraction by chromatography, the identity of Rip-1 has been examined and the results are described herein. This yeast genetic system is based on properties of the Gal-4 protein of the yeast *Saccharomyces cerevisiae*. The Gal-4 protein is a transcriptional activator that is required for the expression of genes encoding enzymes for galactose usage. It is made up of two separable and functionally required domains: an N-terminal which binds to specific DNA sequences (UASg); and the C-terminal domain needed to activate transcription. Two hybrid proteins are made: one is between the binding domain and the known protein, the bait; the other is a hybrid of the activation domain and the unknown expressed from a library of genes. Interaction between the two proteins will restore Gal-4 function. Basically, the interaction of the bait protein with the interacting cellular protein will localize the activation domain close to sites on the DNA for the DNA-binding domain. This is a non-covalent interaction that will lead to the expression of any reporter gene regulated by the Gal-4. Interaction between the bait protein, and the unknown protein is assayed through detection of β-galactosidase production in addition to the selection for histidine production through the His3 reporter gene.

Using the two yeast system, Rip-1 was identified. To identify Rip-1, the bait protein used was Vpr. The interaction of the Vpr from two strains of HIV-1, pNL4-3 and pHxB2, was tested. The difference between the two are: pNL4-3 Vpr is a full length protein encoding for 96 amino acids, where as pHxB2 has a 26 amino acids truncation in the C-terminal region. The truncated version is used as a precaution because there was evidence that the full length Vpr caused cell growth arrest and structural defects in the yeast cell.

PCR of fragment. The Polymerase Chain Reaction was carried out with reagents purchased from Perkin Elmer. The procedure for the PCR was the same for both the pHxb2 and pNL4-3 Vpr, except for the primers used. For this reaction 100 μg of plasmid DNA was added to the mixture of PCR buffer (10 mM Tris-HCl, pH 8.3; 50 mM KCl), 25 mM $MgCl_2$, dNTPs, 2.5 units of Taq polymerase, 20 pmole oligonucleotide primers, and distilled water to the final volume of 100 μL. The cycling conditions for the reaction were 94° C. denaturing for 1 min., 55° C. annealing for 1.5 min., and 72° C. extension for 3 min. The reaction went for 25 cycles. The primers used to amplify Vpr from pHxB2 were: 5'TGGATCCATGGAACAAGCCC AGAAGAC-CAAG3' (sense) (SEQ ID NO:1) and 5'ATGTCGACGC-TATGTCGACACCCAATTCTGAA 3' (antisense) (SEQ ID NO:2). The primers used to amplify Vpr from pNL4-3 were 5'TGGATCCATGG AACAAGCCCAGAAGACCAAG3' (sense) (SEQ ID NO:3) and 5'GGGGATCCTTAG-GATCTCTGGCTC CATTTCT3' (antisense) (SEQ ID NO:4). Unwanted byproducts from the PCR reaction were removed by subjecting the mixture to Qiagen's Qiaquick PCR Purification kit.

Cloning. For cloning both pHxB2 and NL4-3 Vpr(s), the PCR amplified product was run on a 1.2% low melt gel and the 237 base pair fragment was excised and cleaned by phenol-chloroform purification method. This entails adding equal volumes of phenol, then chloroform isoamyl alcohol to the gel fragment suspended in TE. The DNA is precipitated with 2.5 M ammonium acetate and 2 volumes of ethanol. The purified fragment was digested with restriction enzymes BamHl and Sal1; digested fragments were then ligated into the vector already cut with BamHl-Sal1, using T4 ligase from Boehringer Mannheim. The ligated DNA was transformed into Sure competent cells. A negative control of pGBT9 self ligated vector and a positive control of puc19 DNA were also transformed. The transformed competent cells were plated on LB agar plates containing 100 µg.ml ampicillin. DNA was extracted from positive clones using boiling lysis method. Positives containing the 237 fragment were identified by restriction digesting with BamHl and Sal1.

Cloning the pNL4-3 Vpr followed the above method, except that only BamHl site was used. Using the same restriction site for both ends required special treatment of the vector to prevent self ligation of the vector between complementary ends. Phosphates on both ends of the vector were removed using Shrimp Alkaline Phosphatase. After checking for the presence of the 310 pb fragment indicating the presence of the gene in the plasmid, another test was used to check the orientation of the fragment since the complementary ends allowed the fragment to insert in either orientation. This was accomplished by cutting the plasmid at EcoRI sites which is located on both the vector and the fragment. If the orientation is correct 5' to 3', a 207 bp fragment will be released.

Sequencing. Sequencing is necessary to ensure that the fragment is situated correctly. Plasmid DNA containing the Vpr fragment were purified by mini preparations using either Qiagen Plasmid Mini kit or Promega's Wizard kit. DNA concentration was determined using spectrophotometry. DNA preparation for sequencing was accomplished with Applied Biosystem's Taq Dideoxy Terminator Sequencing kit. The reaction mixture included 1 µg of DNA, TACS buffer, AmpliTaq, dNTPs, DNA Binding Domain primer (5' TCATCGGAAGAGAGTAG-3' SEQ ID NO:5), and water up to 20 µL. The mixture was put through 25 cycles that rotated between 96° C., 50° C., and 60° C. The reaction was purified using Boehringer Mannheim's Quick Spin protocol before sequencing at the Cell Center DNA sequencing facility of the University of Pennsylvania. After analysis of the correct clones, they were amplified and purified using Qiagen's Plasmid Maxi kit. This DNA is the Binding Domain hybrid for the Two Hybrid system.

Insertion of the linker. Due to a frame shift caused by the nature of the primer used for the pHxB2 Vpr fragment at the 5' BamHl end, an 8 bp linker had to be inserted. A positive vector was digested at the SmaI site, dephosphorylated, and purified. This vector was then ligated with Xbal linker. The newly ligated plasmid was transformed and purified and sequenced for the presence of the linker.

YEAST SYSTEM

Preparation of the cDNA. The three cDNA libraries to be used were human B-cell, lymphocyte and brain cell. Before transformation into yeast, the efficiency of each library had to be tittered. The plasmid libraries must have >10^8 cfu/ml (colony forming units per ml). The tittering was determined by plating the $E.$ $coli$ colonies at different dilutions and then calculating the cfu/ml based on the number of colonies formed at that particular dilution using a formula that accounted for each of the dilutions made. Next, the libraries were amplified. Amplification is important to obtain enough of all the gene containing plasmids for the transformations. The protocol is simply to plate out approximately 100–150, 150 mm plates of plasmid containing $E.$ $coli$. Colonies were grown over night, scraped from plates and purified using Qiagen Mega Prep kit.

Transformation of Target protein into Yeast. $Saccharomyces$ $cerevisiae$ HF7c reporter host strain was inoculated into a 200 ml culture of YPD (20 g/l Difco peptone, 10 g/l yeast extract) and grown over night, shaking at 30° C. Cells were diluted in the morning and grown until density was between $OD_{600}$ of 0.3–0.4 before transformation began. Cells were pelleted and washed with sterile TE/LiAC (made fresh from stocks of 10× TE [0.1 M Tris-HCl, 0.01 M EDTA, pH 7.5] and 10× LiAc [1 M lithium acetate adjusted to pH 7.5 with dilute acetic acid]). Plasmid DNAs and herring testes carrier DNA were added to competent yeast cells. Next, sterile PEG solution (40% PEG, 1× TE, 1× LiAc, made fresh from stocks of 50% PEG, 10× LiAc, 10×, TE). Tubes were incubated at 30° shaking for 30 minutes. Then, dimethyl sulfoxide was added before the heat pulse for 15 minutes in a 42° C. water bath. The cells were spun down and resuspended in appropriate SD medium (6.7 g/l Difco yeast nitrogen base without amino acids plus solution of amino acids without the ones selected for). They were incubated for 1 hr shaking 30° C. before plating. The plates were incubated at 30° C. until colonies appeared (3–4 days). The positive control used was pCL1 which encodes the wild-type full-length GAL-4 gene.

Identification of Positive Colonies. Colonies from the transformation were replicated onto two fresh SK Trp-, Leu-, His- plates. One of the duplicate plates was then subjected to the β-galactosidase assay. Sterile VWR grade 410 filters were presoaked in a solution of Z buffer/X-gal containing 0.27 ml of β-mercaptoethanol/100 ml. Z buffer consists of $Na_2HPO_4*7H_2O$, $NaH_2PO_2*H_2O$, KCl, and $MgSO_4*7H_2O$. X-gal is made of 5-bromo-4-chloro-3-indolyl-β-D-galactopyranoside in N,N-dimethylformamide at 20 mg/ml. Dry sterile filters were placed over the agar plate containing the transformed colonies. Gentle pressing of the filters transferred the colonies onto the filters. The filters were necessary to make the cell permeable to the Z-buffer/X-gal solution. The thawed filter is then placed on the presoaked filters, cell side up. The filters were cut with the BamH1 enzyme. The some of the colonies even had the gene in the right sense orientation as indicated by the release of the correct size fragment when cut with EcoR1 enzyme. The EcoR1 site is situated in the vector as well as within the Vpr gene. If the insertion was in the sense orientation, a 207 base pair fragment should be cut out. If in the antisense, a different size fragment would result. From the sequence of the plasmid, it was evident that the gene was present.

The second phase of the project is the transformation of the plasmids containing genes for the hybrid proteins into the yeast report strain HF7c. Plasmids may be transformed simultaneously or sequentially, inserting the target binding domain first.

The pGBT9 vector with Vpr genes were transformed into the HF7c yeast with procedure described for in the methods section. Yeast colonies that took up the plasmid were selected by their ability to thrive on plates lacking in tryptophan. While binding domain vector has a gene that codes for tryptophan, activation domain vector has a gene coding for leucine synthesis. Yeast colonies with the binding domain plasmid already inside were then subjected to another round of transformation. In addition, a plasmid containing the activation domain and genes from the cDNA library was introduced. The library we screen the pHxB2 Vpr against was the human PBL'5. Two clues provided the evidence that we may have an interacting protein or proteins to the Vpr from this initial trial. From the many yeast cells we transformed, a few were able to survive on medium lacking tryptophan, leucine, and histidine. As mentioned before, the vectors account for the ability to survive without tryptophan and leucine. However, neither of the vectors can initiate histidine production. Histidine is the first reporter gene for detecting the interaction between the Vpr and the cellular protein. When there is interaction and the Gal4 transcriptional activator is re-established, then transcription for the histidine gene occurs. A second solution was used to assay for β-galactosidase activity. From this trial, we have isolated four positives. These have been formed in expansion assays. The specific gene sequences of the Rip-1 gene have been identified and are attached as SEQ ID NO:6, SEQ ID NO:7, and SEQ ID NO:8.

We claim:

1. A DNA molecule having a nucleotide sequence consisting of less than 4000 nucleotides and comprising a nucleotide sequence selected from the group consisting of: SEQ ID NO:6, SEQ ID NO:7, SEQ ID NO:8, a fragment of SEQ ID NO:6 having at least 100 nucleotides, a fragment of SEQ ID NO:7 having at least 100 nucleotides, and a fragment of SEO ID NO:8 having at least 100 nucleotides.

2. The DNA molecule of claim 1 consisting of up to 1000 nucleotides.

3. A DNA molecule having a nucleotide sequence consisting of less then 4000 nucleotides and comprising SEQ ID NO:6.

4. A DNA molecule having a nucleotide sequence consisting of less then 4000 nucleotides and comprising SEQ ID NO:7.

5. A DNA molecule having a nucleotide sequence consisting of less then 4000 nucleotides and comprising SEQ ID NO:8.

6. The DNA molecule of claim 1 consisting of a nucleotide sequence selected from the group consisting of: SEQ ID NO:6, SEQ ID NO:7, and SEQ ID NO:8.

7. A recombinant vector comprising a nucleotide sequence comprising one or more of: SEQ ID NO:6, SEQ ID NO:7, and SEQ ID NO:8.

8. The recombinant vector of claim 7 comprising SEQ ID NO:6.

9. The recombinant vector of claim 7 comprising SEQ ID NO:7.

10. The recombinant vector of claim 7 comprising SEQ ID NO:8.

11. The recombinant vector of claim 7 comprising SEQ ID NO:6, SEQ ID NO:7, and SEQ ID NO:8.

12. A recombinant host cell comprising a recombinant vector according to claim 7.

13. The recombinant host cell of claim 12 wherein said vector comprises SEQ ID NO:6.

14. The recombinant host cell of claim 12 wherein said vector comprises SEQ ID NO:7.

15. The recombinant host cell of claim 12 wherein said vector comprises SEQ ID NO:8.

16. The recombinant host cell of claim 12 wherein said vector comprises SEQ ID NO:6, SEQ ID NO:7, and SEQ ID NO:8.

17. The DNA molecule of claim 1 comprising a nucleotide sequence selected from the group consisting of: SEQ ID NO:6, SEQ ID NO:7, SEQ ID NO:8.

18. The DNA molecule of claim 6 consisting of SEQ ID NO:6.

19. The DNA molecule of claim 6 consisting of SEQ ID NO:7.

20. The DNA molecule of claim 6 consisting of SEQ ID NO:8.

* * * * *